United States Patent [19]

Higgins et al.

[11] 4,352,755

[45] Oct. 5, 1982

[54] PRODUCTION OF MALEIC ANHYDRIDE

[75] Inventors: Raymond Higgins, Middlesbrough; Graham J. Hutchings, Northallerton; Deborah A. Trebilco, Redcar; Philip E. Starkey, Guisborough, all of England

[73] Assignee: Imperial Chemical Industries Limited, London, England

[21] Appl. No.: 204,699

[22] Filed: Nov. 6, 1980

[30] Foreign Application Priority Data

Nov. 20, 1979 [GB] United Kingdom ............... 7940087

[51] Int. Cl.³ .......................................... C07D 307/60
[52] U.S. Cl. .................................. 549/258; 549/259; 549/260
[58] Field of Search ...................... 260/346.76, 346.75

[56] References Cited

U.S. PATENT DOCUMENTS

| | | | |
|---|---|---|---|
| 3,293,268 | 12/1966 | Bergman et al. | 260/346.75 |
| 3,849,448 | 11/1974 | Crampton et al. | 260/346.75 |
| 3,899,516 | 8/1975 | Dickason | 260/346.75 |
| 3,928,392 | 12/1975 | Cherry et al. | 260/346.75 |
| 3,968,054 | 7/1976 | Cherry et al. | 252/468 |
| 4,062,873 | 12/1977 | Harrison | 260/346.75 |
| 4,085,122 | 4/1978 | Stefani et al. | 260/346.75 |
| 4,094,888 | 6/1978 | Straus | 260/346.75 |
| 4,222,945 | 9/1980 | Higgins et al. | 260/346.75 |

FOREIGN PATENT DOCUMENTS 789414 1/1958 United Kingdom .

*Primary Examiner*—Henry R. Jiles
*Assistant Examiner*—Bernard Dentz
*Attorney, Agent, or Firm*—Cushman, Darby & Cushman

[57] ABSTRACT

Maleic anhydride is produced by oxidizing a straight chain $C_4$ hydrocarbon with oxygen in a stream comprising 25 to 60% by volume of the $C_4$ hydrocarbon, 20 to 45% by volume of oxygen and optionally inert gases to produce a stream containing at least 2½% by volume of maleic anhydride and condensing maleic anhydride substantially free from water from this stream.

10 Claims, No Drawings

PRODUCTION OF MALEIC ANHYDRIDE

THIS INVENTION relates to the production of maleic anhydride.

Maleic anhydride is produced commercially by the oxidation of benzene or straight chain $C_4$ hydrocarbons. Because of the high cost of benzene and the loss of two carbon atoms per molecule in oxidising it to maleic anhydride, the less wasteful oxidation of $C_4$ hydrocarbons to maleic anhydride is increasingly being preferred to the older benzene oxidation process. Among the $C_4$ hydrocarbons n-butane may be preferred to butenes and butadiene because it may be available at fuel value whereas the latter may be used as feedstocks for chemical processes for example producing polymers, copolymers and oligomers and thus have a high alternative use value. Because mixed $C_4$ hydrocarbon streams may be available from crackers at lower cost than their separated components, mixed $C_4$ hydrocarbons may be particularly attractive feedstocks.

In the oxidation of benzene to maleic anhydride it has proved possible to condense at least some maleic anhydride from the product without also condensing water which reacts with maleic anhydride producing maleic acid. However, whereas benzene produces only two moles of water on a stoichiometric basis and the process proceeds at a high selectivity, the $C_4$ hydrocarbon oxidation processes may proceed with lower selectivity, thus producing more water by further oxidation of the feedstock, and produce as well, on a stoichiometric basis, two moles of water using butadiene, three moles of water using an n-butene and four moles of water using n-butane.

Because of the greater production of water in the $C_4$ hydrocarbon oxidation processes at present in use it has been impractical to condense maleic anhydride from the reaction product without also condensing water and thus producing maleic acid. Drying a crude product gas stream has not been practical, because maleic anhydride tends to be removed in drying processes. Since the production of the acid was inevitable, the product has in practise been recovered by scrubbing the product gases with an aqueous solvent, recovering the acid from the solvent and dehydrating the acid to the anhydride when the anhydride was the desired product. The need to supply the demand for the anhydride by dehydration of the acid is a weakness in processes of this type.

It is an object of this invention to provide a process of oxidising $C_4$ hydrocarbons to maleic anhydride in which maleic anhydride is condensed from the reaction product substantially free from water. In the invention, after the recovery of the anhydride as aforesaid, any further anhydride present may be recovered, for example by condensation in the presence of water or by stripping for example with an aqueous solvent, as maleic acid.

The invention comprises producing a gas stream containing at least 2½% by volume maleic anhydride by oxidizing a straight chain $C_4$ hydrocarbon with oxygen in a stream comprising $C_4$ hydrocarbon, 25 to 60% preferably 40 to 55% and more preferably 45 to 50% by volume, oxygen 20 to 45% and preferably 25 to 35% by volume, and optionally inert gases, 0 to 30% preferably 5 to 25% and more preferably 12 to 20% by volume, condensing maleic anhydride substantially free from water from the gas stream comprising at least 2½% by volume maleic anhydride, and optionally then recovering further product as maleic acid from the said stream.

The oxidation may be carried out in the presence of any suitable catalyst, for example, a vanadium containing catalyst, for example a vanadium/molybdenum or preferably a vanadium/phosphorus mixed oxide catalyst. When butenes are used a vanadium/titanium catalyst may for example by employed.

It is preferred to produce a gas stream comprising at least 3% and preferably at least 4% by volume of maleic anhydride.

If desired, after recovering further product as maleic acid, the gas stream may be cooled further in order to condense any unconverted $C_4$ hydrocarbons which may then, if desired, be recycled to the process. Carbon dioxide and any permanent gases for example nitrogen then remain and may, if desired, be partially fed to the oxidation stage as they constitute suitable inert gases. It is preferred that at most 2% $v/v$ and more preferably at most 1% $v/v$ of carbon monoxide and preferably at most 5% $v/v$ water vapour and more preferably at most 1% $v/v$ water vapour is present in the oxidation stage.

It is preferred that the stream comprising the $C_4$ hydrocarbon and oxygen which is fed to the oxidation stage should comprise carbon dioxide as this may improve the selectivity of the catalyst.

It is preferred to recover at least 60% of the maleic anhydride substantially free from water by condensation but it is normally possible to condense more than this in a substantially water-free state. It is generally found that a substantial amount of maleic anhydride can be condensed as a liquid which makes removal from the condenser easy.

The gas compositions encountered in the course of this invention appear at all times to lie outside the flammable limits; nonetheless it is desirable that precautions should be taken against the occurrence of flammable conditions in the course of the process.

The oxidation stage may be carried out for example at temperatures in the range 250°–600° C., preferably 300°–500° C. and at pressures in the range 0.5–10 bars absolute and preferably 1 to 3 bars absolute. The condensation of maleic anhydride substantially free from water may be achieved by cooling of the product gas to a temperature exceeding the dewpoint of water at the concentration of water in the exit gases.

Recovery of further product as maleic acid from the product gas stream may be carried out by scrubbing the stream preferably with an aqueous solvent.

EXAMPLE

A vanadium/phosphorus mixed oxide catalyst was prepared as follows:

Vanadium pentoxide (60.6 g) and concentrated aqueous hydrochloric acid (790 ml) were refluxed with stirring for one hour. To this solution orthophosphoric acid (88% 50.9 ml) was added and the solution refluxed for a further hour. A portion of solvent (600 ml) was then removed by side arm distillation and a further 200 ml of concentrated aqueous hydrochloric acid was added. The resulting solution was refluxed for a further period of about 1½ hours. The solution was then evaporated to dryness and the resulting solid dried in an oven at 115° C. The resulting solid was boiled with water (20 mls/g solid) for about 2½ hours and the resulting suspension was filtered hot, washed with a small amount of warm water and dried in an air oven. A portion of the dried solid was then ball milled in cyclohexane in the presence of 2% by weight of the solid of an organic comb graft copolymer (poly 12-hydroxystearic acid (molecular weight about 1800)/ethyl acrylate/dimethyl aminoethyl methacrylate: 50/45/5) for 144 hours. The grey solid was recovered and dried at about 90° C. A portion of this was mixed with a pelleting agent sold under the trade name "Sterotex" (3% by weight) and pelletised under a pressure of 16 tons in$^{-2}$. The pellet was crushed to give granules of size 500–710μ. The particles were dried at 150° C. and were then impregnated with an isobutanol solution containing lanthanum nitrate as La(NO$_3$)$_3$.6H$_2$O (14 g per 100 ml) to give a catalyst was La:V ratio 0.027:1. After drying, a 5 ml portion was charged to a tubular fixed bed reactor and the catalyst was calcined in situ by heating at 380° C. at a rate of 9° C./min whilst a 1.5 v/v n-butane/air mixture flowed through the bed at a gas hourly space velocity (GHSV) of 1000 hr$^{-1}$.

A gaseous feed comprising 1.3 v/v n-butane in air was then passed through the catalyst bed at 385° C. at a GHSV of 3000 hr$^{-1}$. The exit gases emerging from the reactor at 1 atm absolute pressure were shown to contain 0.51% by volume maleic anhydride.

The composition of the exit gas stream is such that no significant proportion of the maleic anhydride may be condensed in a substantially anhydrous state.

A gaseous feed comprising about 51% by volume n-butane, 31% by volume oxygen and the remainder essentially carbon dioxide was then fed through the catalyst bed at a GHSV of 750 hr$^{-1}$, the bed being maintained at 380° C. The exit gases emerging from the reactor at 1 atmosphere pressure absolute were shown to contain in excess of 3% by volume maleic anhydride in the presence of less than 25% by volume water vapour.

Maleic anhydride may be recovered in the following manner.

The exit gases are cooled to a temperature of 65° C. enabling at least 75% of the crude maleic anhydride to be directly condensed substantially in the absence of water. By this method 0.75 mole of maleic anhydride is recovered directly per liter of catalyst per hour.

A gaseous feed comprising about 46% by volume n-butane, 35% by volume oxygen, the remainder being essentially carbon dioxide, was then passed through the catalyst bed at a GHSV of 1000 hr$^{-1}$ and the catalyst bed was maintained at 381° C. The exit gases emerging at one atmosphere absolute were shown to contain greater than 4% by volume maleic anhydride in the presence of less than 25% by volume water vapour, allowing for molar volume expansion on reaction. This corresponds to a fractional molar conversion of n-butane of approximately 0.15 and a fractional molar selectivity to maleic anhydride based on converted butane of approximately 0.65.

Maleic anhydride may be recovered as follows:

The emergent gases are cooled to 65° C. enabling at least 75% of the crude maleic anhydride to be directly condensed substantially in the absence of water. By this method greater than 1.0 mole of maleic anhydride is recovered directly per liter of catalyst per hour.

We claim:

1. A process which comprises producing a product gas stream containing at least 3% by volume of maleic anhydride by oxidising a straight chain C$_4$ hydrocarbon with oxygen in a stream comprising C$_4$ hydrocarbon 25 to 60% and oxygen 20 to 45%, the percentages being by volume and condensing maleic anhydride substantially free from water from the product gas stream.

2. A process as claimed in claim 1 in which inert gas is present in a concentration of at most 30% by volume in the stream comprising the C$_4$ hydrocarbon.

3. A process as claimed in claim 1 in which the stream comprising the C$_4$ hydrocarbon comprises 40 to 55% by volume thereof.

4. A process as claimed in claim 1 in which the stream comprising the C$_4$ hydrocarbon comprises 25 to 35% by volume of oxygen.

5. A process as claimed in claim 1 in which a gas stream comprising at least 4% by volume of maleic anhydride is produced.

6. A process as claimed in claim 1 in which maleic acid is recovered from the product gas stream after maleic anhydride has first been recovered from the stream.

7. A process as claimed in claim 6 in which unconverted C$_4$ hydrocarbon is condensed from the gas stream after recovery of maleic acid.

8. A process as claimed in claim 1 in which at most 5% by volume of water vapour is present during the oxidation of the C$_4$ hydrocarbon.

9. A process as claimed in claim 2 in which carbon dioxide is present during the oxidation of the C$_4$ hydrocarbon.

10. A process as claimed in claim 1 which is carried out at a temperature in the range of 250° to 600° C. at a pressure in the range 0.5 to 10 bars absolute.

* * * * *